(12) United States Patent
Garcia et al.

(10) Patent No.: US 6,852,547 B2
(45) Date of Patent: Feb. 8, 2005

(54) DYNAMICALLY FORMED ROTORS FOR LOCK-IN AMPLIFIER DETECTION

(75) Inventors: Antonio A. Garcia, Chandler, AZ (US); Mark Hayes, Gilbert, AZ (US); Anil Vuppu, Tempe, AZ (US); Karl Booksh, Gilbert, AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 10/633,352

(22) Filed: Aug. 1, 2003

(65) Prior Publication Data

US 2004/0126903 A1 Jul. 1, 2004

Related U.S. Application Data

(60) Provisional application No. 60/400,235, filed on Aug. 1, 2002.

(51) Int. Cl.[7] ............... G01N 33/48; G01N 33/53; G01N 33/543; G01N 33/566; G01N 35/00
(52) U.S. Cl. ............... 436/526; 436/43; 436/63; 436/501; 436/510; 436/518; 436/523; 436/524; 436/525; 436/536; 424/9.1; 422/50; 422/52; 422/55; 422/58; 422/68.1; 422/81; 422/82; 422/82.05; 422/82.07; 422/82.08; 422/100; 422/101

(58) Field of Search ............... 436/43, 63, 501, 436/510, 518, 523, 524, 525, 526, 536; 424/9.1; 422/50, 52, 55, 58, 68.1, 81, 82, 82.05, 82.07, 82.08, 100, 101

(56) References Cited

U.S. PATENT DOCUMENTS

| | | | | |
|---|---|---|---|---|
| 4,725,140 A | * | 2/1988 | Musha | 356/336 |
| 5,222,808 A | * | 6/1993 | Sugarman et al. | 366/274 |
| 5,817,458 A | * | 10/1998 | King et al. | 435/5 |
| 6,586,259 B1 | * | 7/2003 | Mahan et al. | 436/518 |
| 6,764,859 B1 | * | 7/2004 | Kreuwel et al. | 436/178 |

* cited by examiner

*Primary Examiner*—Jill Warden
*Assistant Examiner*—Brian Sines
(74) *Attorney, Agent, or Firm*—Pitney Hardin LLP

(57) ABSTRACT

A method for measuring low levels of a substance in a sample includes the formation of a rotor from paramagnetic particles in a substantially uniform magnetic field. The rotor is rotated by rotating the substantially uniform magnetic field. A portion of the substance in a sample is bound to the paramagnetic particles, and a signal having a time-varying component is detected. The signal is then processed using a lock-in amplifier with a reference signal having a frequency twice that of the rotation of the magnetic field. This improves the signal-to-noise ratio of the time-varying component of the signal.

10 Claims, 3 Drawing Sheets

DYNAMICALLY FORMED ROTORS FOR LOCK-IN AMPLIFIER DETECTION

CROSS-REFERENCE TO RELATED APPLICATION

This application is based upon U.S. Patent Application Ser. No. 60/400,235, a provisional application, filed Aug. 1, 2002, on which a claim for domestic priority is made.

BACKGROUND OF THE INVENTION

1. Field of the Invention

The present invention relates generally to the field of in vitro diagnostics. More particularly, the present invention relates to the measurement of attomole concentrations in biological assays within nanoliter-to-subnanoliter scale fluid volumes using such diagnostics.

2. Description of the Prior Art

The current in vitro diagnostics (IVD) market has been estimated to be eighteen billion dollars (U.S.) annually. The key market segments are immunoassay and clinical chemistry, with the immunoassay market being much more profitable for IVD companies.

In today's market, automated immunoassays can detect concentrations in the low attomole range; can provide results in from twenty to thirty minutes; and can be produced at low cost, namely, $0.35 per test. Current assays can give results using several hundred microliters of specimen and achieve low attomole detection using chemiluminescence or fluorescence detection in a solid-phase format. In order to develop an ultrasmall device for the same assay using only tens to hundreds of nanoliters of sample, depending upon analyses concentration, sensitivity of detection will need to be significantly improved. This is particularly the case for immunoassays as no equivalent of PCR (polymerase chain reaction) exists for the target amplification of an antigen. Therefore, very sensitive and inexpensive detection systems must be developed for point-of-care devices.

A central challenge, then, is to increase the sensitivity and accuracy of immunoassays within nanoscale volumes. Since the higher sensitivity systems employ high surface area solid-phase systems with light signals for detection, an alternative approach may be made with fluorescence immunoassays using particles. Many fluorophore labels, lasers and light collection systems have been developed to increase fluorescent assay sensitivity. Among the important strategies used to enhance sensitivity and accuracy are the reduction of background fluorescence using longer-lived fluorophores combined with time resolution of fluorescence detection. In addition, fluorophores emitting at a longer wavelength may be used so that light of shorter wavelength from common background fluorescence sources may be filtered out. Finally, materials with minimal fluorescence may be used in the analysis chambers and filters.

These efforts presuppose that care is taken to eliminate background binding from non-specific adsorption or entrainment from incomplete washing of the fluorescent labeled antibody or antigen. Regardless of the care taken to eliminate stray light or the inherent fluorescence of material on the surface or in solution, if the signal being measured is present due to an errant binding of the labeled antigen or antibody, these efforts will be for naught. Moreover, economic and technical drawbacks and limitations also exist for the alternative strategies noted in the preceding paragraph.

Clearly, a technique by which the signal-to-noise ratio for measurement of the foregoing type in nanoscale volumes could be improved would have great benefit in the IVD market. Such a technique is provided by the present invention.

SUMMARY OF THE INVENTION

Accordingly, in its broadest form, the present invention is a method for measuring low levels of a substance in a sample. The method includes the steps of dispersing a plurality of paramagnetic particles in a colloidal solution and introducing an amount of the colloidal solution into a sample chamber.

The sample chamber is subsequently subjected to a substantially uniform magnetic field to form at least one substantially linear structure from the plurality of paramagnetic particles.

A sample having low levels of the substance to be measured is introduced into the sample chamber for analysis. The substantially uniform magnetic field is then rotated at a constant rate to cause said substantially linear structure to rotate therewith. A portion of the substance to be measured in said sample becomes bound to the substantially linear structure.

While the magnetic field is rotating, signals having a time-varying component originating from the sample chamber are detected. These signals are processed with a lock-in amplifier to measure the time-varying component by improving the signal-to-noise ratio thereof using a reference signal having a frequency twice that of the rotation of the substantially uniform magnetic field as a multiplier to measure the low levels of the substance to be measured.

The present invention will now be described in more complete detail with frequent reference being made to the figures identified below.

DETAILED DESCRIPTION OF THE PREFERRED EMBODIMENTS

Figure 1:
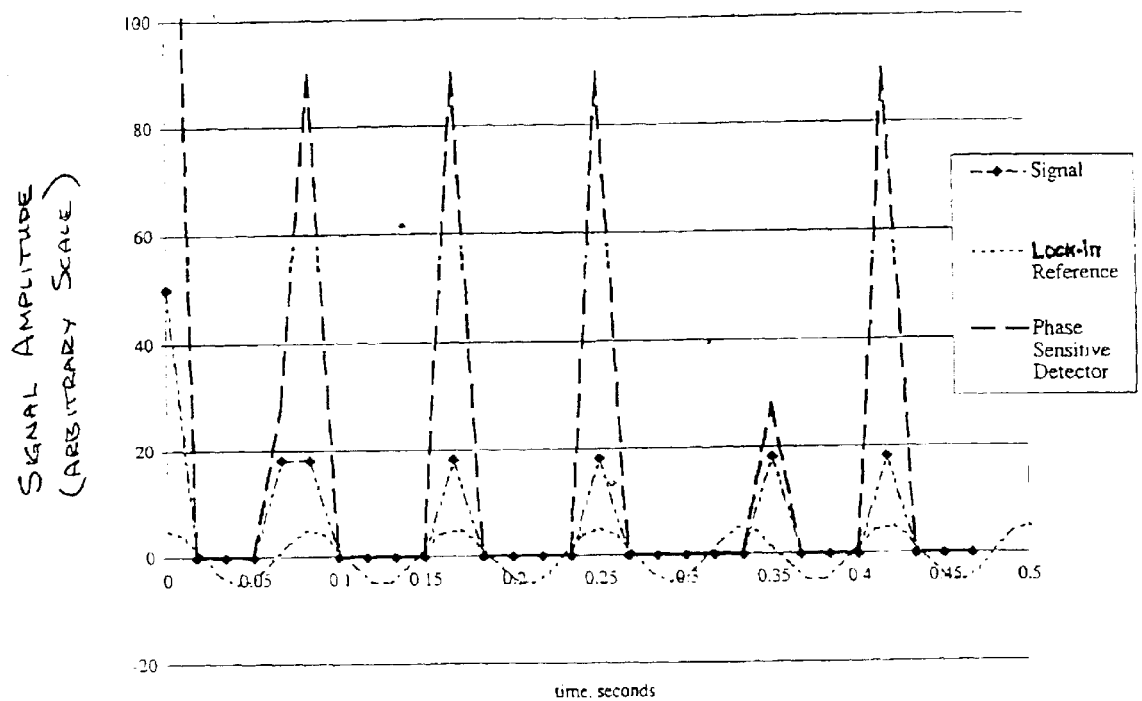
FIG. 1 is a plot illustrating the lock-in amplifier principle as applied to the measurement of fluorescence from a rotating rotor.

Paramagnetic particles are widely used in automated immunoassay because they can be dispersed as colloids in solution and manipulated or collected using a magnetic field. These particles are also readily functionalized by immobilization of antibodies or antigens prior to or during analysis. Recently, it has been demonstrated that magnetic fields can also pattern paramagnetic particles within microchannels and that these patterns can retain their form during liquid flow. It has also been demonstrated that magnetic fields can be used to line up the paramagnetic particles to form linear structures oriented parallel to the direction of the magnetic field. These structures can then be rotated within nanoliter volumes of fluid by rotating the magnetic field.

The structures, which may be referred to as rotors, may be formed in accordance with the teachings of International Publication No. WO 01/89985 A2, the teachings of which are incorporated herein by reference. The subject matter disclosed therein is commonly assigned with that of the present application to the Arizona Board of Regents. Briefly, the paramagnetic particles, which may be obtained from Polysciences, Inc. of Warrington, Pa., U.S.A., and from other vendors, have diameters in a range from 1 micron to 2 microns and a polystyrene surface matrix with amine groups.

When suspended in colloidal solution and subjected to a magnetic field, the paramagnetic particles, each behaving like a small magnet when subjected to the field, become oriented in the direction of the field. In a short time, the paramagnetic particles assume the form of a linear structure by lining up end-to-end with one another due to mutual magnetic forces. Such linear structures may ultimately reach a length of 80 microns or more. Surprisingly, these linear structure can then be induced to rotate in solution by rotating the magnetic field, such as, for example, by rotating the permanent magnet used to line up the paramagnetic particles, without breaking up. Therein lies the basis for the present invention.

In brief, the present invention comprises the alignment of very small magnetizable particles to form a linear structure, which may be rod-like or spiral in form and should not be taken to be strictly linear, the linear structure being referred to as a rotor or microrotor; spinning the rotors using a rotating magnetic field; and processing signals coming from or generated due to this spinning structure to enhance signal-to-noise and to filter background noise. When used within a microchannel, the rotors open new applications in detection within nanoliter-to-subnanoliter scale fluid volumes. The principal of lock-in-amplifiers is used as part of the present invention in a detection strategy to greatly improve the signal-to-noise ratio, thereby to increase detection sensitivity in environmental and biological assays for rapid, miniaturized systems. For immunometric assays, this strategy may lead to quantitative point-of-care devices that are highly sensitive, while yielding a large dynamic range. The technique may also be used for a variety of sensing applications including, but not limited to, chemical detectors, biological contamination detection, and chemical and biowarfare agent monitoring.

A very useful signal that can be monitored from the spinning rotor is fluorescence. Fluorescent emissions from the rotor can be generated by attaching organic fluorescent molecules, quantum dots, fluorescent particles, and other materials. Control and sensitivity of detection make fluorescence detection very desirable. Fluorescence is a well-known signal-generating method and much effort has been devoted to incorporating fluorescence detection into miniaturized and microchip systems.

While the present invention is being described in connection with the measurement of signals caused by fluorescence, it should be understood that other signal-generating methods could be used within the context of the present invention without departing from its scope. For example, other signal generation and detection methods may include, but are not limited to, magnetic property fluctuations, such as magnetoresistance, amperometric and voltametric methods, phosphorescence, other spatially resolved spectroscopic measurements, and inertial fluctuations. The present invention, then, may be practiced using any of these methods as that by which the signal to be measured is physically generated.

When using fluorescence as the method by which the signals of interest are generated, the present invention involves the enhancement of the signals of interest, that is, fluorescence from molecules bound to the rotating rotors, relative to background signals or noise. Essentially, the signal from the rotating rotors is periodic, namely, it is sinusoidally varying, while the background noise is constant. As the rotors are rotating at a frequency identical to that at which the magnetic field is rotating, which is the rate, for example, at which the permanent magnet is being rotated, the signal, viewed, for example, in the plane of rotation, generated by the rotors varies sinusoidally at a frequency double that of the rotation. In short, the signal coming from the rotors is boosted electronically by multiplication with a lock-in reference signal, having a frequency double that of the rotation, to separate the signal of interest from the background noise and to boost the signal-to-noise ratio.

Figure 2:
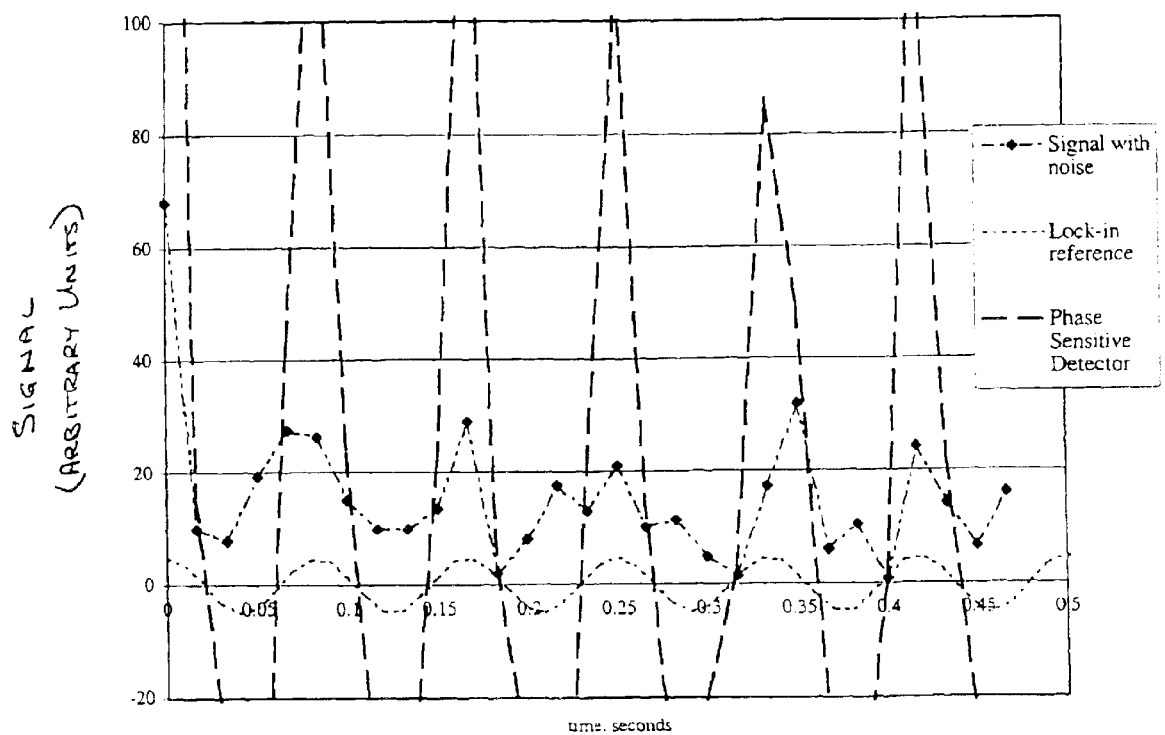
FIG. 2 is a similar plot illustrating the same principle with the presence of background noise.

Reference is now made to FIGS. 1 and 2 for a simple illustration of the lock-in amplifier principle. The fluorescence measured is due to the binding of fluorescent particles to the surface of the paramagnetic particles forming the rotors, simulating the type of signal that can be generated in an immunometric assay with the fluorescent particles representing the label on the secondary antibody. By multiplying a sinusoidal lock-in reference signal, based on twice the rotational frequency of the magnetic field, a dramatic phase-sensitive detector DC output shown as dashed dark lines in FIG. 1 is obtained. The DC output can then be filtered using a low-pass filter, and further processed by adding a second phase-sensitive detector to generate a dual-phase lock-in yielding amplitude and phase angle information.

The dramatic benefits of phase-sensitive detection for weak signals with noise are illustrated in FIG. 2. In this simple example, random noise of up to 100% of the signal is added to the original signal. After phase-sensitive detection, the DC output yields maxima at nearly the same times as seen in FIG. 2, showing the inherent capability of the technique to yield positive readings even in the present of a significant level of noise.

The key technological issue in the employment of detectors and diagnostics is the accuracy and validity of the readings. As shown in FIGS. 1 and 2, rotors, or microrotors, are advantageous over simply measuring the fluorescence from a specific spot or the entire field by tracking how the signal-to-noise ratio can be boosted. Moreover, sensitivity issues aside, much effort is also spend on avoiding overshoot or false positive readings. While this can be caused by non-specific targeting or binding, it also can be due to taking readings near the level where the signal is at the same level as the noise. The invention described here can help minimize there false readings by expanding the detector range while filtering the background noise.

Out of the myriad immunoassay and related sensing techniques, the present invention offers several advantages over other methods. A solid-phase assay is employed to pre-concentrate the analyte by confining it to the surface of paramagnetic particles through high affinity, antibody/antigen interactions. Antigen capture by immobilized antibodies is advantageous for sensitivity and quantitation, and thus many commercial systems use this as the basis of clinical and research immunoassays. While solid-phase capture offers this significant benefit, diffusion to a surface and boundary layers can pose kinetic limitations. In the present invention, this pitfall is virtually eliminated by creating a significant level of convective mass transfer of analyte and other reagents to the particle surface. Laminar flow into the sample chamber, while stirring within the chamber using a rotating magnetic field, creates substantial mixing. While fluid motion is in the laminar region, it is believed that there is three-dimensional fluid mixing around the particle surface confining diffusional path lengths to very small distances within the rotor boundary layer. Mixing also refreshes the surface layer frequently and maintains high driving forces for mass transfer to and from the particle surface.

Besides advantages in isolation and separation, the present invention also confers advantages in detection. Lock-in signal amplification is well known to improve detection sensitivities in many systems by a hundredfold. More specifically, control over the frequency of the fluorescent signal being acquired so that background fluorescence can be filtered via signal processing is inherent in the present invention. Moreover, light detection could also acquire sinusoidal signals from several independent rotors, all rotating in phase, thus simplifying operation and potentially improving reliability by interrogating more than one signal source. Decoupling the signal from the noise created by the background of bulk fluid and chamber material fluorescence results in a simple method for troubleshooting. Enhancements of this benefit can also be obtained by conducting lock-in amplification at different rotor rotational speeds. Internal reflectance of light within microchannels can be a troublesome source of noise, but, by using a lock-in amplifier, this source can be virtually eliminated without resorting to complex arrays of filters, sophisticated light sources or optics, or simply being limited by a high level of noise.

As noted above, the present invention employs a lock-in amplifier method for detecting the fluorescent signal from a rotor controlled by a varying magnetic field. The rotor is created by patterning paramagnetic particles using a strong magnetic field and by controlling field orientation with respect to the analyte volume, particle size and particle concentration. The rotor speeds may be in a range from 5 rpm to 600 rpm. Rotor lengths using 1-micron particles may be from 20 to 80 microns. The light being emitted from fluorescent molecules on the rotor can be tracked using a lock-in amplifier using the reference signal which is externally controlled by the speed at which the magnetic field is rotated. All background fluorescence not coming from the surface of the particles on the rotor is filtered out.

Lock-in amplifiers are well known to measure the amplitude and phase of signals buried in noise. They achieve this by acting as a narrow bandpass filter that removes much of the unwanted noise while allowing the signal which is to be measured to pass through. In fluorescence immunoassay, noise is generated primarily from background fluorescence of the solution and/or the container, and from non-specific binding of the signal-producing antibody or antigen. The present invention relies upon detecting the light emitted from paramagnetic particles patterned and rotating in a sub-nanoliter chamber using a lock-in amplifier. The frequency of the signal to be measured and hence the passband region of the filter is set by the rotating magnetic field acting as a reference signal, which is supplied to the lock-in amplifier along with the signal being measured. In the present invention, measurements could be speeded up by allowing data acquisition before the washing step that is routinely used to remove unbound signal antibody or antigen, these producing a signal that would become part of the noise whose effect is reduced by the practice of the invention.

It is also important to note that particles patterned into rotors do not show an appreciable phase shift relative to the rotating magnetic field in an aqueous solution. Viscous drag, however, does have an effect in viscous solutions, such as glycerol-water mixtures, but the resulting phase shift can be corrected for.

Several examples of the present invention will now be described, although it should be understood that the invention is not to be considered limited to these examples.

In each example, the sample-analysis chamber is a trench below a flow microchannel where paramagnetic particles, sample and reagent solutions can be introduced by flow. The analysis chamber can be pre-filled with hundreds to thousands of paramagnetic particles by a sequence of steps combining flow and patterning resulting in a rod-like assembly, that is, the rotor. The rotors may range in length from 20 to 80 microns. The sample chamber has angled walls which trap the rotor at the bottom thereof to keep it from escaping through the flow channel as a consequence of the tendency of the rotor to grow lengthwise in an appropriately oriented magnetic field. The design of the sample chamber provides great flexibility in sample chamber volume and microchannel dimensions. Sample chamber volumes from picoliters to nanoliters can be accommodated. It is also important to note that the number of active sites available for detection in a typical rotor can also be varied with the particles on the surface having sites usually on the order of $1 \times 10^6$ active sites per particle, which is equivalent to about $1 \times 10^7$ sites per square micrometer of exposed particle area. High surface densities of active antibody on the surface of the rotor can increase the amount of antigen capture and hence improve detection sensitivity.

Three examples of lock-in amplifier systems to detect fluorescent signals are given in FIGS. 3A, 3B, 4 and 5. Each includes an excitation source, such as a light-emitting diode (LED) or laser, and appropriate optical filtering, which are not shown. Miniature mirroring and filtering systems for fluorescence measurements in microscopy and chips can be integrated with the examples.

In the most sensitive type of assay, the immunometric or so-called sandwich immunoassay, a secondary antibody containing the fluorescent signal is introduced so that detection can occur after it binds to the captured antigen. However, because the fluorescent molecules are present in solution and are usually non-specifically bound to the surface of the chamber as well as specifically and possibly non-specifically bound to the surface of the particles, extensive washing is normally required. When the signal from the rotating particles is used in the lock-in amplifier system, the light noise emitted by the fluorescent molecules in solution or by molecules bound to the walls of the chamber will be substantially filtered out by the low pass filter. The trajectory of non-magnetic fluorescent particles resembles a random walk when the magnetic field is rotating as the rotor drags the fluid in a circular motion. Such motion is of a frequency that is filtered out by the lock-in amplifier. Moreover, loosely held fluorescent antibody molecules not specifically bound to captured antigen can be removed by vigorous mixing of the rotors. The detection schemes may allow the accurate measurement in shorter analysis times than those normally called for in assays that rely on washing.

The approach of the present invention is similar to a basic lock-in amplifier system that can be split into four stages: an input gain stage, the reference circuit, a demodulator and a low-pass filter. For the input gain stage, a photomultiplier tube serves the high performance amplifier task of variable gain input stage preprocessing the signal by amplifying it to a level suitable for the demodulator. The reference circuit or signal is merely the externally controlled rotating magnetic field converted to a sinusoidal signal. Phase shifting is a relatively inconsequential 0.3 degrees or less. In a lock-in amplifier, the demodulator is a multiplier which takes the input signal and the reference and multiplies them together.

As the input signal to be measured and the reference signal are of the same frequency, the difference frequency is zero and a DC output proportional to the amplitude of the input signal and the cosine of the phase different between the signals, which cosine is essentially equal to one, is obtained. The noise signals will still be present at the output of the demodulator and may have very large amplitudes. However, as the various noise components on the input signal are at different frequencies compared to the reference signal, the sum and difference frequencies will be non-zero and will not contribute to the DC level of the output signal. This DC level, which is proportional to the input signal, can finally be recovered by passing the output from the demodulator through a low-pass filter.

Figure 3A:
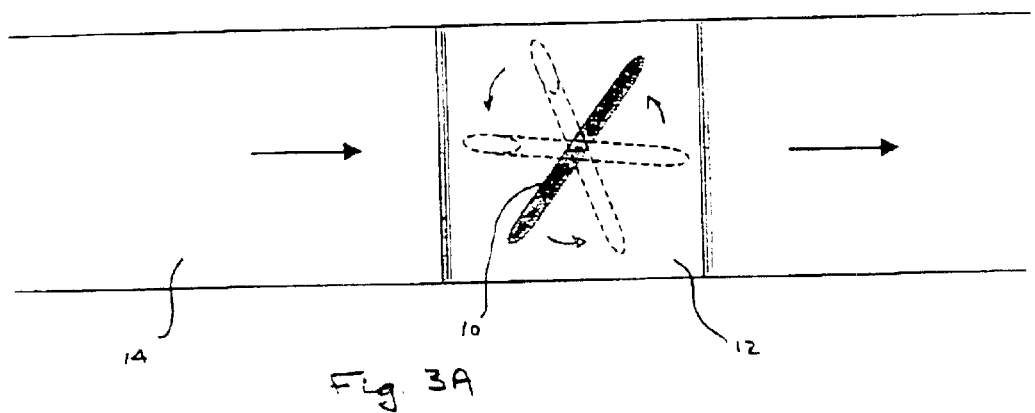
FIG. 3A is a top plan view of a measurement set-up for a first embodiment of the present invention.
Figure 3B:
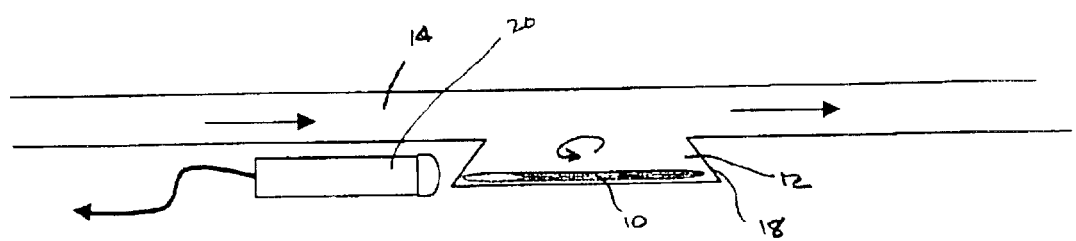
FIG. 3B is a side view of the set-up shown in FIG. 3A.

Referring now to FIGS. 3A and 3B for a first embodiment of the present invention, wherein FIG. 3A is a top plan view of a microchannel and a sample chamber, and FIG. 3B is a side view thereof, paramagnetic particles are formed into a rotor 10 within the sample chamber 12 below the microchannel 14. A rotating magnetic field, caused for example by a spinning permanent magnet, spins the rotor 10 at a rate equal to that at which it is being spun. The angled walls 18 of the sample chamber 12 tend to keep the rotor 10 in the sample chamber 12. Fluorescence emission from the rotor 10 undergoes a sinusoidal variation when spinning based on the orientation of the light detector assembly 20, which includes lenses, a photomultiplier tube (PMT) or a photodiode. LED's, not shown, are used to excite the fluorophores. The rotor surface can be used in fluorescence-based assays by well-established solid-phase assay techniques in immunology, molecular biology and environmental science.

Figure 4:
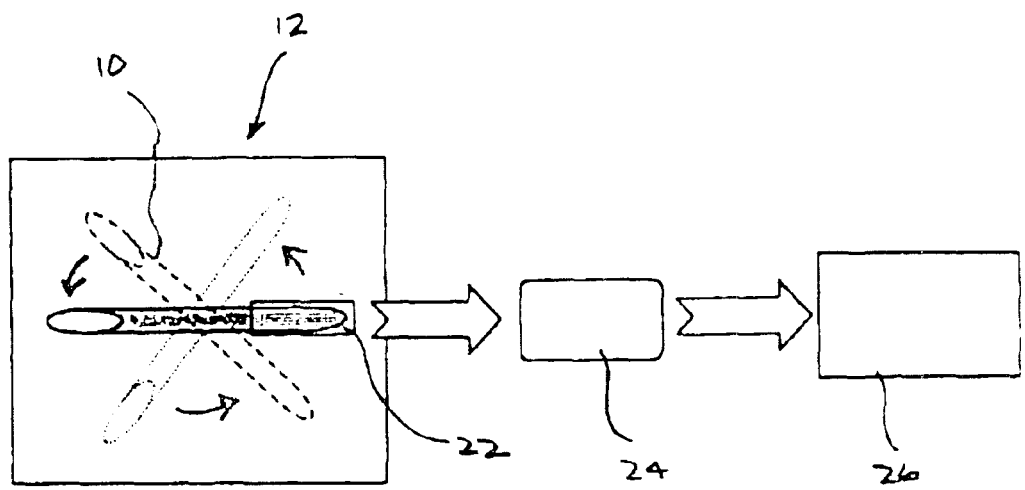
FIG. 4 is a top view of a sample chamber in a second embodiment of the present invention.

FIG. 4 is a top view of a sample chamber 12 in a second embodiment. The sample chamber 12 has a dark or reflective coating with a window 22 (or slit). Again, the rotor 10 rotates at the same frequency as the magnetic field. The window 22 (or slit) allows a time varying light signal, which generates a periodic signal waveform, to pass therethrough. The collected light is amplified using a photomultiplier tube 24 before sending the signal to a lock-in amplifier 26. LED or laser source and optical methods to excite particle surfaces and filter the excitation light are not shown.

Figure 5:
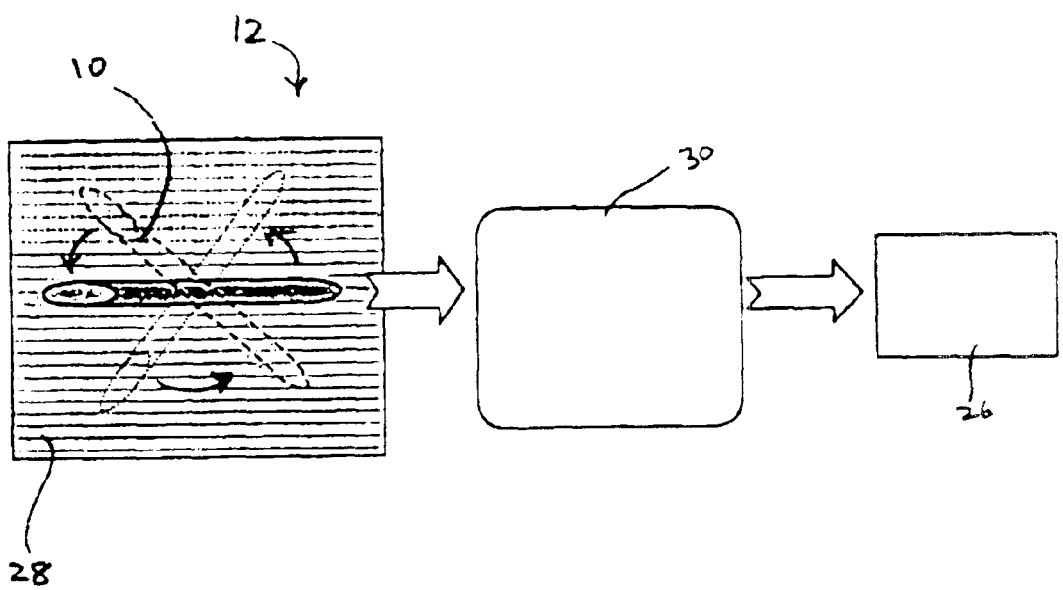
FIG. 5 is a top view of a sample chamber in a third embodiment of the present invention.

FIG. 5 is a top view of a sample chamber 12 in a third embodiment. The sample chamber 12 is covered with a charge-coupling device (CCD) 28, which enables an alternate signal collection using spatial interpretation of time-varying CCD images to generate a signal waveform at converter 30. The rotating magnetic field is converted to a reference signal that is fed to the lock-in amplifier 26. LED or laser source and optical methods to excite particle surfaces and filter the excitation light are not shown.

Modifications of the above would be obvious to those of ordinary skill in the art, but would not bring the invention so modified beyond the scope of the appended claims.

What is claimed is:

1. A method for measuring low levels of a substance in a sample, said method comprising the steps of:
    dispersing a plurality of paramagnetic particles in a colloidal solution;
    introducing an amount of said colloidal solution into a sample chamber;
    subjecting said sample chamber to a substantially uniform magnetic field;
    forming at least one substantially linear structure from said plurality of paramagnetic particles with said substantially uniform magnetic field;
    introducing a sample having low levels of said substance to be measured into said sample chamber for analysis;
    rotating said substantially uniform magnetic field at a constant rate to cause said substantially linear structure to rotate therewith;
    binding a portion of said substance to be measured in said sample to said substantially linear structure;
    detecting signals having a time-varying component originating from said sample chamber; and
    processing said signals with a lock-in amplifier to measure said time-varying component by improving the signal-to-noise ratio thereof using a reference signal having a frequency twice that of the rotation of said substantially uniform magnetic field as a multiplier to measure said low levels of said substance to be measured.

2. A method as claimed in claim 1 wherein said paramagnetic particles are coated with amine groups, and wherein said substance to be measured in said sample binds with said amine groups.

3. A method as claimed in claim 1 further comprising the step of exposing said sample chamber to an excitation source.

4. A method as claimed in claim 3 wherein said excitation source is a light source.

5. A method as claimed in claim 4 wherein said light source is a laser.

6. A method as claimed in claim 4 wherein said light source is a light-emitting diode (LED).

7. A method as claimed in claim 4 wherein said signals having a time-varying component are detected with a photomultiplier (PM) tube.

8. A method as claimed in claim 4 wherein said signals having a time-varying component are detected with a charge-coupling device (CCD).

9. A method as claimed in claim 1 wherein said substantially uniform magnetic field is generated by a permanent magnet.

10. A method as claimed in claim 9 wherein said substantially uniform magnetic field is rotated by rotating said permanent magnet.

* * * * *